US012781282B2

(12) United States Patent
Gu

(10) Patent No.: US 12,781,282 B2
(45) Date of Patent: Nov. 3, 2026

(54) BIOMARKER COMBINATIONS FOR DIAGNOSIS OF DILATED CARDIOMYOPATHY AND DIAGNOSTIC KITS THEREFOR

(71) Applicant: Ye Gu, Wuhan City (CN)

(72) Inventor: Ye Gu, Wuhan City (CN)

( * ) Notice: Subject to any disclaimer, the term of this patent is extended or adjusted under 35 U.S.C. 154(b) by 0 days.

(21) Appl. No.: 19/407,151

(22) Filed: Dec. 3, 2025

(65) Prior Publication Data

US 2026/0234726 A1 Aug. 13, 2026

(30) Foreign Application Priority Data

Feb. 11, 2025 (CN) ......................... 202510149661.9

(51) Int. Cl.

*C12Q 1/6883* (2018.01)
*G01N 33/68* (2006.01)

(52) U.S. Cl.

CPC ....... *C12Q 1/6883* (2013.01); *G01N 33/6887* (2013.01); *C12Q 2600/158* (2013.01); *C12Q 2600/178* (2013.01); *G01N 2333/70503* (2013.01); *G01N 2440/14* (2013.01); *G01N 2474/10* (2021.08); *G01N 2800/325* (2013.01)

(58) Field of Classification Search

CPC ............ C12Q 1/6883; C12Q 2600/158; C12Q 2600/178; G01N 33/6887; G01N 2333/70503; G01N 2440/14; G01N 2474/10; G01N 2800/325

See application file for complete search history.

(56) References Cited

PUBLICATIONS

Cheng et al., Clin. Transl. Med., 13: e1258, 1-21, Feb. 4, (Year: 2023).*

* cited by examiner

*Primary Examiner* — Cynthia B Wilder
(74) *Attorney, Agent, or Firm* — troutman pepper locke; Tim Tingkang Xia, Esq.

(57) ABSTRACT

This invention relates to a biomarker combination, diagnostic kits and methods for diagnosis of dilated cardiomyopathy, and use of the biomarker combination in preparation of the diagnostic kits for dilated cardiomyopathy. The biomarker combination comprises miR-126-5p and a tyrosine phosphorylation level of PECAM-1 proteins, wherein an expression level of miR-126-5p is upregulated in patients with dilated cardiomyopathy, and the tyrosine phosphorylation level of PECAM-1 protein is increased in the patients with the dilated cardiomyopathy.

10 Claims, 4 Drawing Sheets

Specification includes a Sequence Listing.

BIOMARKER COMBINATIONS FOR DIAGNOSIS OF DILATED CARDIOMYOPATHY AND DIAGNOSTIC KITS THEREFOR

SEQUENCE LISTING

This application includes a Sequence Listing in the XML file that is electronically submitted via EFS-Web on Dec. 3, 2025. The XML file contains a sequence listing entitled "269588.000003_Sequence_Listing.xml" created on Aug. 6, 2025 and is 8,647 bytes in size. The Sequence Listing contained in this 269588.000003_Sequence_Listing.xml file is part of the specification and is hereby incorporated by reference herein in its entirety.

CROSS-REFERENCE TO RELATED PATENT APPLICATION

This application claims priority to and the benefit of Chinese Patent Application Serial No. 202510149661.9, filed Feb. 11, 2025, which is incorporated herein in its entirety by reference.

FIELD OF THE INVENTION

This invention relates generally to disease diagnosis, and more particularly to a combination of biomarkers for the diagnosis of dilated cardiomyopathy and their applications, and diagnostic kits for dilated cardiomyopathy.

BACKGROUND OF THE INVENTION

Dilated cardiomyopathy (DCM) is the common type of cardiomyopathy, characterized by unilateral or bilateral ventricular enlargement and decreased systolic function. The causes of DCM are numerous, but the etiology of some cases remains unclear. Its clinical manifestations are highly variable, and diagnosis is usually in the middle to late stages. Different studies report a one-year mortality rate ranging from 10% to 50%, making early detection and diagnosis of DCM crucial for clinical significance.

miRNAs are small non-coding RNAs that regulate post-transcriptional gene expression. Studies have shown that some miRNAs are abnormally expressed in tumors or other diseases. Detecting miRNAs through tissue biopsy is highly invasive, especially obtaining heart and lung tissue for testing, which is impractical. Therefore, detecting miRNAs in a patient's blood has some diagnostic value for diseases such as tumors.

Existing literature reports the association of various miRNAs with heart diseases, and some reports suggest miRNAs as biomarkers for DCM, but their diagnostic efficacy is poor. Therefore, developing biomarkers with high specificity and sensitivity for the diagnosis of DCM is of great importance.

SUMMARY OF THE INVENTION

To address the problems existing in the art, this invention discloses a biomarker combination for the diagnosis of dilated cardiomyopathy, its applications, and a diagnostic kit for the dilated cardiomyopathy. This biomarker combination and the diagnostic kit exhibit high sensitivity and specificity when used for the detection of the dilated cardiomyopathy.

The technical solution of this invention to solve the above-mentioned technical problems is as follows:

In one aspect, the invention relates to a biomarker combination for the diagnosis of the dilated cardiomyopathy, wherein the biomarker combination includes miR-126-5p and a tyrosine phosphorylation level of PECAM-1 protein. The expression level of miR-126-5p is upregulated in patients with the dilated cardiomyopathy, and the tyrosine phosphorylation level of PECAM-1 protein is increased in patients with the dilated cardiomyopathy.

In one embodiment, the biomarker combination further includes PECAM-1 mRNA, the expression level of which is downregulated in patients with the dilated cardiomyopathy.

In one embodiment, the biomarker combination is derived from peripheral blood endothelial cells.

In another aspect, the invention relates to an application of the biomarker combination in preparation of the diagnostic kit for the dilated cardiomyopathy.

In a further aspect, the invention relates to a diagnostic kit for the dilated cardiomyopathy, comprising a first diagnostic reagent and a second diagnostic reagent. The first diagnostic reagent is used to detect the expression level of miR-126-5p, and the second diagnostic reagent is used to detect the tyrosine phosphorylation level of PECAM-1 protein.

In one embodiment, the first diagnostic reagent comprises a primer pair designed for amplifying the cDNA reverse-transcribed from miR-126-5p, wherein the primer pair comprises a forward primer and a reverse primer, the base sequence of the forward primer is shown in SEQ ID NO. 3, and the reverse primer is a universal reverse amplification primer with the base sequence shown in SEQ ID NO. 4. The second diagnostic reagent comprises a PECAM-1 protein isolation and purification reagent and a Western blotting (protein immunoblotting) assay reagent containing anti-phosphorylated tyrosine antibodies.

In one embodiment, the dilated cardiomyopathy diagnostic kit further includes one or more of a peripheral blood endothelial cell isolation and extraction reagent, an RNA extraction reagent, an RNA reverse transcription reagent, and a real-time quantitative PCR reagent.

In one embodiment, the peripheral blood endothelial cell isolation and extraction reagent includes an antibody/magnetic bead conjugate complex. The antibody/magnetic bead conjugate complex is prepared by conjugating a CD45 antibody and a CD31 antibody with magnetic beads, respectively.

In one embodiment, the dilated cardiomyopathy diagnostic kit further includes a first internal control reagent for detecting the expression level of miR-126-5p and a second internal control reagent for detecting the tyrosine phosphorylation level of PECAM-1 protein.

In one embodiment, the internal control reagent for detecting the expression level of miR-126-5p is an U6 gene, and the internal control reagent for detecting the tyrosine phosphorylation level of PECAM-1 protein is a β-actin.

In one embodiment, the dilated cardiomyopathy diagnostic kit further includes a third detection reagent for detecting PECAM-1 mRNA.

In one embodiment, the dilated cardiomyopathy diagnostic kit further includes a third internal control reagent for detecting an expression level of PECAM-1 mRNA.

In one embodiment, the internal control reagent for detecting an expression level of PECAM-1 mRNA is GAPDH.

In yet a further aspect, the invention relates to a diagnostic kit for detecting dilated cardiomyopathy in a subject. The diagnostic kit comprises (a) a primer set configured to amplify cDNA corresponding to miR-126-5p; (b) an antibody-based reagent configured to detect tyrosine-phosphorylated PECAM-1 protein; and (c) an endothelial cell isolation reagent comprising magnetic beads conjugated to antibodies that bind CD45 and CD31.

In one embodiment, the antibody-based reagent comprises a monoclonal antibody that binds a phosphotyrosine epitope of PECAM-1.

In one embodiment, the kit further comprises primers configured to amplify PECAM-1 mRNA.

In one embodiment, the kit further comprises an internal control primer set for U6 or GAPDH.

In one embodiment, the kit further comprises a reagent for quantifying total PECAM-1 protein.

In one aspect, the invention relates to an article of manufacture comprising instructions for measuring, in peripheral blood endothelial cells, miR-126-5p expression, PECAM-1 mRNA expression, or PECAM-1 protein tyrosine phosphorylation to diagnose dilated cardiomyopathy; and at least one reagent configured to perform the measurement.

In one embodiment, the article further comprises a real-time PCR reagent for detecting miR-126-5p.

In one embodiment, the instructions specify that elevated miR-126-5p and increased PECAM-1 protein phosphorylation are indicative of dilated cardiomyopathy.

In another aspect, the invention relates to a method for diagnosing dilated cardiomyopathy in a subject. The method comprises measuring, in endothelial cells isolated from peripheral blood of the subject, (i) an expression level of miR-126-5p and (ii) a tyrosine phosphorylation level of PECAM-1 protein; and optionally (iii) an expression level of PECAM-1 mRNA, and determining that the subject has dilated cardiomyopathy when the miR-126-5p expression level is elevated relative to that of a control, the PECAM-1 mRNA expression level is reduced relative to the control, and the tyrosine phosphorylation level of PECAM-1 protein is increased relative to that of the control.

In one embodiment, the endothelial cells are isolated magnetic bead capture of CD45-positive leukocytes and magnetic bead capture of CD31-positive cells.

In one embodiment, detecting the tyrosine phosphorylation level of PECAM-1 protein comprises performing Western blot analysis using an anti-phosphotyrosine antibody.

In one embodiment, the method further comprises generating a logistic regression score based on the measured biomarkers and classifying the subject as having dilated cardiomyopathy when the score exceeds a predetermined threshold.

In one embodiment, the miR-126-5p expression level is increased by at least 4.0-fold relative to a healthy control.

In one embodiment, the PECAM-1 mRNA level is reduced by at least 30% relative to a healthy control.

In one embodiment, the miR-126-5p expression level, PECAM-1 mRNA level, and PECAM-1 tyrosine phosphorylation level are reported as a ratio relative to internal controls selected from U6, β-actin, and GAPDH.

In yet another aspect, the invention relates to another method for diagnosing dilated cardiomyopathy in a subject. The method comprises detecting in peripheral blood endothelial cells of the subject: (a) an elevated level of miR-126-5p; and (b) an increased tyrosine phosphorylation level of PECAM-1 protein; wherein the concurrent presence of the elevated miR-126-5p level and the increased PECAM-1 protein phosphorylation level indicates the subject has dilated cardiomyopathy.

In one embodiment, the PECAM-1 phosphorylation level is at least 1.4-fold greater than that of a normal control.

To the inventor's best knowledge, it is for the first time discovered, through extensive research and exploration in the dilated cardiomyopathy, that miR-126-5p and the tyrosine phosphorylation level of PECAM-1 protein, or miR-126-5p and the tyrosine phosphorylation level of PECAM-1 protein combined with PECAM-1 mRNA, can be used as a combination of biomarkers for highly sensitive and specific detection of the dilated cardiomyopathy, and can be applied to the preparation of diagnostic reagents or kits for the dilated cardiomyopathy. The diagnostic kit for the dilated cardiomyopathy prepared using miR-126-5p and the tyrosine phosphorylation level of PECAM-1 protein as a biomarker combination shows a sensitivity of about 86.2% and a specificity of about 96.8%, respectively; while the diagnostic kit for the dilated cardiomyopathy prepared using miR-126-5p, PECAM-1 mRNA, and the tyrosine phosphorylation level of PECAM-1 protein as biomarkers shows a sensitivity of about 93.1% and a specificity of about 93.7%, respectively.

These and other aspects of the present invention will become apparent from the following description of the preferred embodiment taken in conjunction with the following drawings, although variations and modifications therein may be affected without departing from the spirit and scope of the novel concepts of the invention.

BRIEF DESCRIPTION OF THE DRAWINGS

The accompanying drawings illustrate one or more embodiments of the invention and together with the written description, serve to explain the principles of the invention. Wherever possible, the same reference numbers are used throughout the drawings to refer to the same or like elements of an embodiment.

DETAILED DESCRIPTION OF THE INVENTION

Figure 1:
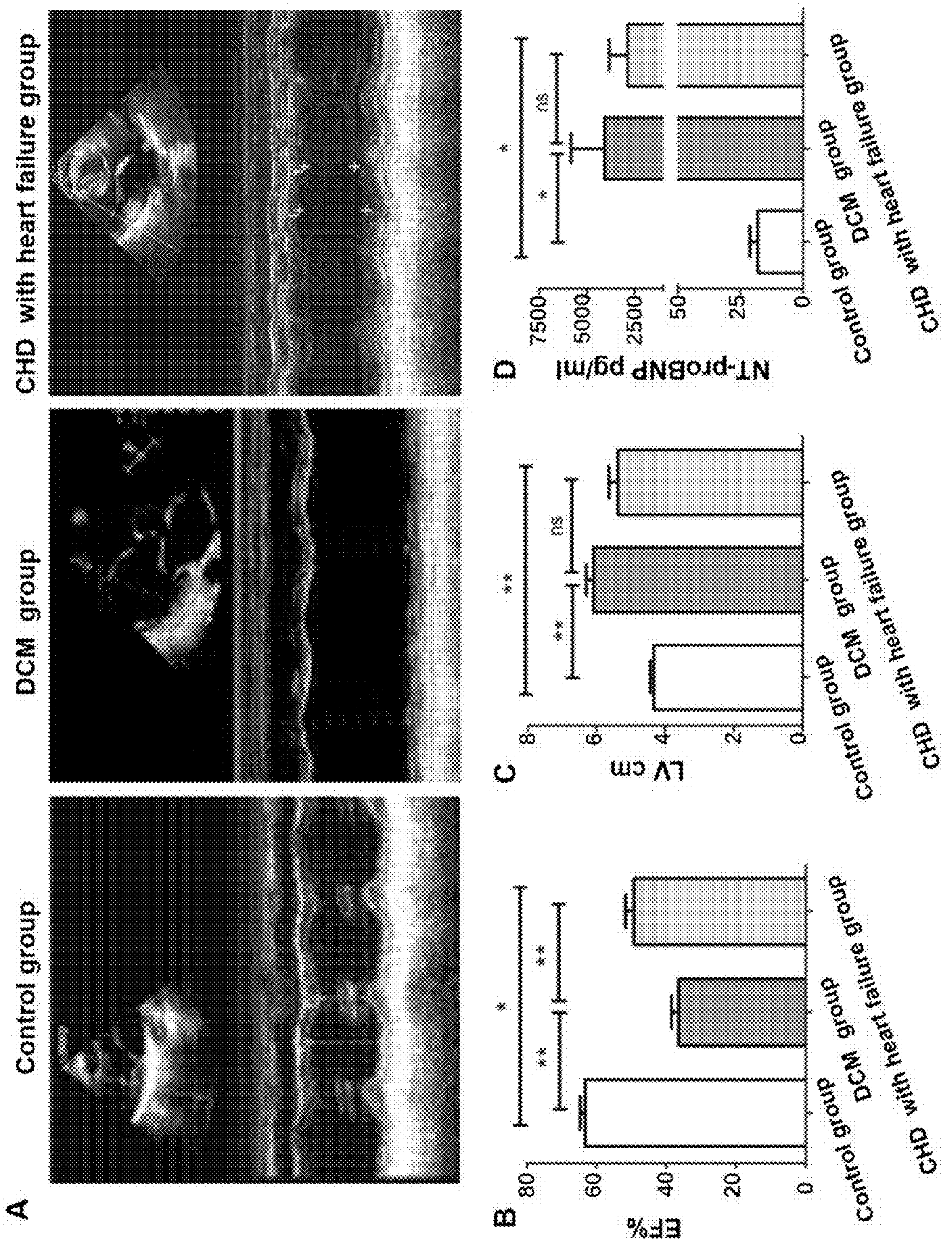
FIG. 1 shows the cardiac function-related data of the dilated cardiomyopathy group, the coronary heart disease and heart failure group, and the control group according to Embodiment 1 of the invention. Panel A: cardiac ultrasound images. Panel B: the cardiac ejection fraction (EF). Panel C: the left ventricular diameter (LV). Panel D: the serum NT-proBNP.

The invention will now be described more fully hereinafter with reference to the accompanying drawings, in which exemplary embodiments of the invention are shown.

However, this invention may be embodied in many different forms and should not be construed as limited to the embodiments set forth herein. Rather, these embodiments are provided so that this specification will be thorough and complete and fully convey the invention's scope to those skilled in the art.

The terms used in this specification generally have their ordinary meanings in the art, within the context of the invention, and in the specific context where each term is used. Certain terms used to describe the invention are discussed below, or elsewhere in the specification, to provide additional guidance to the practitioner regarding the description. For convenience, certain terms may be highlighted, for example using italics and/or quotation marks. The use of highlighting has no influence on the scope and meaning of a term; the scope and meaning of a term are the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that, as used in the description herein and throughout the claims that follow, the meaning of "a", "an", and "the" includes plural reference unless the context clearly dictates otherwise. Also, it will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, or section without departing from the invention's teachings.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation depicted in the figures. For example, if the device in one of the figures. is turned over, elements described as being on the "lower" side of other elements would then be oriented on "upper" sides of the other elements. The exemplary term "lower", can, therefore, encompasses both an orientation of "lower" and "upper," depending on the particular orientation of the figure. Similarly, if the device in one of the figures is turned over, elements described as "below" or "beneath" other elements would then be oriented "above" the other elements. Therefore, the exemplary terms "below" or "beneath" can encompass both an orientation of above and below.

It will be further understood that the terms "comprises" and/or "comprising," or "includes" and/or "including" or "has" and/or "having", or "carry" and/or "carrying," or "contain" and/or "containing," or "involve" and/or "involving, and the like are to be open-ended, i.e., to mean including but not limited to. When used in this specification, they specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this specification, and will not be interpreted in an idealized or overly formal sense unless expressly so defined herein.

As used in this specification, "around", "about", "approximately" or "substantially" shall generally mean within 20 percent, preferably within 10 percent, and more preferably within 5 percent of a given value or range. Numerical quantities given herein are approximate, meaning that the term "around", "about", "approximately" or "substantially" can be inferred if not expressly stated.

As used in this specification, the phrase "at least one of A, B, and C" should be construed to mean a logical (A or B or C), using a non-exclusive logical OR. As used herein, the term "and/or" includes any and all combinations of one or more of the associated listed items.

The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in a different order (or concurrently) without altering the principles of the invention.

Arterial endothelial cells are important components of vascular functions, widely distributed in the endothelial wall of blood vessels. They play a crucial role in pathological and physiological activities regulating vasoconstriction/vasodilation, maintaining blood supply to target tissues, phagocytosis, and foreign body removal.

miR-126-5p, as a non-coding RNA, is widely expressed in the arterial endothelial cells. It is formed by the primary transcript, Pri-miRNA, of endothelial cells forming a stem-loop structure under the action of RNA polymerase II, which is then processed into a miRNA precursor (Pre-miRNA) by the Drosha-DGCR8 complex, and finally processed into miRNA by the Dicer enzyme (RNAase III) in the cytoplasm. In certain tumor diseases, miR-126a-5p is abnormally expressed in the cytoplasm and mediates the signal transduction and biological functions of downstream target genes.

The inventor conducted extensive and in-depth research on the dilated cardiomyopathy and discovered that on one hand, under oxidative stress, platelet-endothelial cell adhesion molecule-1 (PECAM-1) plays a related molecular signal transduction function. PECAM-1 undergoes molecular conformational changes, and the protein tyrosine phosphorylation reaction is multiplied. Through downstream molecular signal cascade transduction, endothelial apoptosis and necrosis occur, leading to microarterial blood flow attenuation, eventually resulting in myocardial ischemia, cardiac enlargement, and heart failure. On the other hand, the inventor discovered in the research on the gene regulatory pathway of miR-126-5p that PECAM-1 mRNA is a target gene of miR-126-5p. Under the oxidative stress, the expression of miR-126-5p in the cytoplasm is upregulated. Overexpressed miR-126-5p inhibits the transcription and translation of PECAM-1, and thus the expression of PECAM-1 mRNA is reduced. In patients with the dilated cardiomyopathy, the combined effects of the overexpression of miR-126-5p and the effect of the multiplication of the tyrosine phosphorylation of PECAM-1 protein under the oxidative stress lead to myocardial ischemia following microartery endothelial injury, ultimately resulting in cardiac enlargement and heart failure.

Compared to non-dilated cardiomyopathy patients (e.g., healthy individuals and patients with coronary artery disease), patients with clinical dilated cardiomyopathy show a tyrosine phosphorylation multiplication of PECAM-1 protein in the peripheral blood endothelial cells, accompanied by a significant increase in miR-126-5p. miR-126-5p regulates PECAM-1 expression, leading to decreased expression of PECAM-1 mRNA and the membrane protein PECAM-1. Therefore, the tyrosine phosphorylation level of PECAM-1 protein combined with miR-126-5p, or the tyrosine phosphorylation level of PECAM-1 protein combined with miR-126-5p and PECAM-1 mRNA, can be used as a biomarker combination for the detection of dilated cardiomyopathy.

In some exemplary embodiments, the biomarker combination is of miR-126-5p and the tyrosine phosphorylation level of PECAM-1 protein. This biomarker combination is used to prepare a diagnostic reagent or kit for the dilated cardiomyopathy. This reagent or kit, by detecting miR-126-5p and the tyrosine phosphorylation level of PECAM-1 protein, distinguishes between dilated cardiomyopathy patients and healthy individuals, as well as between dilated cardiomyopathy patients and healthy individuals and patients with coronary heart disease.

In some exemplary embodiments, the biomarker combination is of miR-126-5p, PECAM-1 mRNA and the tyrosine phosphorylation level of PECAM-1 protein. This biomarker combination is used to prepare a diagnostic reagent or kit for dilated cardiomyopathy. This reagent or kit, by detecting miR-126-5p, PECAM-1 mRNA and the tyrosine phosphorylation level of PECAM-1 protein, distinguishes between dilated cardiomyopathy patients and healthy individuals, as well as between dilated cardiomyopathy patients and healthy individuals and patients with coronary heart disease.

All the above biomarkers are derived from peripheral blood endothelial cells.

In some exemplary embodiments, the endothelial cells are isolated from peripheral blood, total RNA is extracted, and then cDNA is synthesized by reverse transcription targeting miR-126-5p and PECAM-1 mRNA, respectively. The expression levels of miR-126-5p and PECAM-1 mRNA relative to the internal control are detected using quantitative real-time PCR.

Specifically, peripheral blood mononuclear cells (PBMCs) are isolated from whole blood, and endothelial cells are extracted from PBMCs using CD45/CD31 antibody-conjugated magnetic beads. To address the issue of low endothelial cell counts below the detection limit, the peripheral blood endothelial cell samples are concentrated. In one embodiment, the concentration is 10-fold. Then, miR-126-5p and PECAM-1 mRNA in peripheral blood endothelial cells are detected. It is found that miR-126-5p expression in the peripheral blood endothelial cells from patients with the dilated cardiomyopathy is significantly higher than that in normal controls, while PECAM-1 mRNA levels are significantly lower than those in normal controls.

The endothelial cells are isolated from peripheral blood, total protein is extracted, and the tyrosine phosphorylation level of PECAM-1 protein in the endothelial cells is detected using Western blotting. Specifically, the endothelial cells are lysed, and the tyrosine phosphorylation of PECAM-1 protein in human peripheral blood is detected using a protein expression analysis system (such as the Bio-Rad protein expression analysis system) with specific antibodies. It is found that the tyrosine phosphorylation level of PECAM-1 protein in the peripheral blood endothelial cells of patients with the dilated cardiomyopathy (PECAM-1 protein tyrosine phosphorylation gray value/internal reference β-actin gray value) is significantly higher than that of the normal control group. Compared to the normal control group, the tyrosine phosphorylation level of PECAM-1 protein in the peripheral blood endothelial cells of patients with the dilated cardiomyopathy is 1.4 to 3.5 times of that of the normal control group.

In one aspect, the invention also provides a diagnostic kit for the dilated cardiomyopathy, comprising a first diagnostic reagent and a second diagnostic reagent. The first diagnostic reagent is used to detect the expression level of miR-126-5p, and the second diagnostic reagent is used to detect the tyrosine phosphorylation level of PECAM-1 protein.

In some embodiments, the first diagnostic reagent includes a primer pair designed for amplifying the cDNA reverse-transcribed from miR-126-5p. The primer pair includes a forward primer and a reverse primer. The base sequence of the forward primer is shown in SEQ ID NO. 3, and the reverse primer is a universal reverse amplification primer with the base sequence shown in SEQ ID NO. 4. The second diagnostic reagent includes a PECAM-1 protein isolation and purification reagent and a protein immunoblotting (Western blotting) assay reagent containing anti-phosphorylated tyrosine antibodies.

In some embodiments, in addition to the above-disclosed first and second diagnostic reagents, the diagnostic kit for the dilated cardiomyopathy also includes one or more of a peripheral blood endothelial cell isolation and extraction reagent, an RNA extraction reagent, an RNA reverse transcription reagent, and a real-time quantitative PCR reagent.

In some embodiments, the peripheral blood endothelial cell isolation and extraction reagent includes an antibody/magnetic bead conjugate complex, which is prepared by conjugating CD45 and CD31 antibodies with magnetic beads, respectively. Optionally, the peripheral blood endothelial cell isolation and extraction reagent may also include a PBMC (Peripheral Blood Mononuclear Cell) isolation buffer, a PBS (Phosphate-Buffered Saline) buffer, and/or a PBST (Phosphate Buffered Saline with Tween-20) elution buffer.

In some embodiments, the RNA extraction reagent includes a lysis buffer, proteinase K, a protein removal buffer, a washing buffer, genomic DNA removal columns, RNase-free adsorption columns, RNase-free double-distilled water, and/or DEPC (diethyl pyrocarbonate) water.

In some embodiments, the protein immunoblotting assay reagent containing anti-phosphorylated tyrosine antibodies includes a RIPA (Radioimmunoprecipitation Assay) protein lysis reagent, Western spectroscopy and transfer reagents, a specific antibody against tyrosine phosphorylation of PECAM-1 protein, and an elution buffer, secondary antibody incubation, and developing reagents for protein expression analysis.

In some exemplary embodiments, the specific antibody against tyrosine phosphorylation of PECAM-1 protein used is Tyr20.

In some exemplary embodiments, an assay reagent capable of detecting internal controls is also included. Optionally, the internal control for miR-126-5p is U6, the internal control for tyrosine phosphorylation of PECAM-1 protein is β-actin, and the internal control for PECAM-1 mRNA is GAPDH.

In yet a further aspect, the invention relates to a diagnostic kit for detecting dilated cardiomyopathy in a subject. The diagnostic kit comprises (a) a primer set configured to amplify cDNA corresponding to miR-126-5p; (b) an antibody-based reagent configured to detect tyrosine-phosphorylated PECAM-1 protein; and (c) an endothelial cell isolation reagent comprising magnetic beads conjugated to antibodies that bind CD45 and CD31.

In some embodiments, the antibody-based reagent comprises a monoclonal antibody that binds a phosphotyrosine epitope of PECAM-1.

In some embodiments, the kit further comprises primers configured to amplify PECAM-1 mRNA.

In some embodiments, the kit further comprises an internal control primer set for U6 or GAPDH.

In some embodiments, the kit further comprises a reagent for quantifying total PECAM-1 protein.

In one aspect, the invention relates to an article of manufacture comprising instructions for measuring, in peripheral blood endothelial cells, miR-126-5p expression, PECAM-1 mRNA expression, or PECAM-1 protein tyrosine phosphorylation to diagnose dilated cardiomyopathy; and at least one reagent configured to perform the measurement.

In some embodiments, the article further comprises a real-time PCR reagent for detecting miR-126-5p.

In some embodiments, the instructions specify that elevated miR-126-5p and increased PECAM-1 protein phosphorylation are indicative of dilated cardiomyopathy.

In another aspect, the invention relates to a method for diagnosing dilated cardiomyopathy in a subject. The method comprises measuring, in endothelial cells isolated from peripheral blood of the subject, (i) an expression level of miR-126-5p and (ii) a tyrosine phosphorylation level of PECAM-1 protein, and optionally (iii) an expression level of PECAM-1 mRNA; and determining that the subject has dilated cardiomyopathy when the miR-126-5p expression level is elevated relative to that of a control, the PECAM-1 mRNA expression level is reduced relative to the control, and the tyrosine phosphorylation level of PECAM-1 protein is increased relative to that of the control.

In some embodiments, the endothelial cells are isolated by sequential removal of magnetic bead capture of CD45-positive leukocytes and magnetic bead capture of CD31-positive cells. For example, CD45 antibody binds to leukocytes, and the resulting positive complex is captured by magnetic beads. The magnetic bead complex precipitate is then removed by adsorption using a magnetic rack.

In some embodiments, detecting the tyrosine phosphorylation level of PECAM-1 protein comprises performing Western blot analysis using an anti-phosphotyrosine antibody.

In some embodiments, the method further comprises generating a logistic regression score based on the measured biomarkers and classifying the subject as having dilated cardiomyopathy when the score exceeds a predetermined threshold.

In some embodiments, the miR-126-5p expression level is increased by at least 4.0-fold relative to a healthy control.

In some embodiments, the PECAM-1 mRNA level is reduced by at least 30% relative to a healthy control.

In some embodiments, the miR-126-5p expression level, PECAM-1 mRNA level, and PECAM-1 tyrosine phosphorylation level are reported as a ratio relative to internal controls selected from U6, β-actin, and GAPDH.

In yet another aspect, the invention relates to another method for diagnosing dilated cardiomyopathy in a subject. The method comprises detecting in peripheral blood endothelial cells of the subject: (a) an elevated level of miR-126-5p; and (b) an increased tyrosine phosphorylation level of PECAM-1 protein; wherein the concurrent presence of the elevated miR-126-5p level and the increased PECAM-1 protein phosphorylation level indicates the subject has dilated cardiomyopathy.

In some embodiments, the PECAM-1 phosphorylation level is at least 1.4-fold greater than that of a normal control.

The invention provides, among other things, at least the following novel features and advantages Discovery of a new multi-marker combination uniquely diagnostic for dilated cardiomyopathy (DCM): The invention identifies, for the first time, a specific combination of biomarkers that reliably diagnose DCM, wherein the biomarkers include (i) miR-126-5p expression level (upregulated in DCM), and (ii) tyrosine phosphorylation level of PECAM-1 protein (significantly increased in DCM), and optionally (iii) PECAM-1 mRNA expression level (significantly decreased in DCM). The three-marker signature (miR-126-5p ↑, PECAM-1 mRNA ↓, PECAM-1-P-Tyr ↑) is not disclosed in the prior art as a combined diagnostic rule for DCM.

Novel mechanistic insight connecting miR-126-5p, PECAM-1 mRNA suppression, and PECAM-1 phosphorylation: The invention identifies: (a) PECAM-1 mRNA as a direct target gene of miR-126-5p; (b) oxidative stress-induced hyper-phosphorylation of PECAM-1 protein in endothelial cells; and (c) the combined dysregulation as a specific molecular signature of DCM rather than general heart failure. This mechanistic connection appears newly discovered.

Novel use of peripheral blood endothelial cells as the source of these markers: The biomarker trio is characterized specifically from peripheral blood endothelial cells, not plasma or cardiac tissue. The cell isolation method is non-obvious and allows robust detection even with low endothelial cell counts.

Novel diagnostic kits implementing these markers: The kit combines specialized reagents: (1) primer pairs for miR-126-5p and PECAM-1 mRNA, (2) magnetic-bead endothelial cell isolation (CD45- and CD31-bead system), and (3) reagents for Western blot detection of phosphorylated PECAM-1 (e.g., Tyr20 antibody). The specific kit composition has not been previously disclosed as a unified diagnostic product for DCM.

High diagnostic sensitivity and specificity for DCM: The multi-marker panel significantly outperforms single biomarkers previously reported.

Enables early-stage DCM detection: The panel differentiates: DCM vs. healthy individuals; and DCM vs. (coronary heart disease+heart failure), with high accuracy earlier than imaging-based methods.

Minimally invasive (blood-based) approach: Avoids tissue biopsy and cardiac sampling.

Easily integrated into clinical workflows: PCR-based detection+Western blot-based phosphorylation analysis+ magnetic-bead isolation are all standard lab techniques.

Expandable kit framework: Allows addition or removal of markers while maintaining diagnostic power.

The invention as a whole is nonobvious for several reasons:

Prior art biomarkers for DCM are known to be low-performance: Prior studies observed inconsistent relationships between single miRNAs and DCM, with poor diagnostic power. The invention recognizes that a multi-marker signature involving phosphorylation states, not just gene expression, is necessary.

No prior teaching or suggestion to combine: a miRNA (miR-126-5p), mRNA (PECAM-1), and post-translational modification (PECAM-1 tyrosine phosphorylation), as a composite diagnostic signature for DCM.

Unexpected improved diagnostic performance: The combination yields unexpectedly high sensitivity and specificity: (a) about 86-97% for the 2-marker panel, (b) about 93% for the 3-marker panel, and (c) AUC up to 0.981, significantly exceeding single-marker systems. Such performance constitutes an unexpected technical effect.

Non-obvious selection of peripheral blood endothelial cells and a multi-step isolation technique: The process solves the problem of low endothelial cell yields and preserves integrity of RNA and phospho-proteins.

Novel mechanistic reasoning underlying marker selection: The invention uncovered a dual mechanism: miR-126-5p suppresses PECAM-1 mRNA, oxidative stress amplifies PECAM-1 phosphorylation, and creating a distinct biochemical pattern specific to DCM. Such insight would not be obvious to one skilled in the art.

Without intent to limit the scope of the invention, exemplary instruments, apparatus, methods, and their related results according to the embodiments of the invention are given below. In the following embodiments, unless otherwise specified, experimental methods without specific conditions are generally performed under conventional conditions, such as referring to “Molecular Cloning: A Laboratory Manual” (3rd edition), edited by J. Sambrook et al., published by Science Press. Specific experimental conditions can be determined through simple experiments if necessary. PCR amplification experiments are performed according to the reaction conditions provided by the plasmid or DNA template supplier or the kit instructions, and adjustments could be made through simple experiments if necessary. Unless otherwise specified, all materials and reagents used in the following examples are commercially available.

Embodiment 1

Based on the 2023 European Society of Cardiology Cardiomyopathy Guidelines for dilated cardiomyopathy, clinical baseline data are collected from 32 patients diagnosed with dilated cardiomyopathy and 32 patients diagnosed with coronary heart disease (CHD) with heart failure between December 2023 and October 2024. Blood samples are collected in the morning on an empty stomach. Simultaneously, 30 healthy individuals are randomly selected as a control group, and their clinical baseline data are also included. Echocardiography, coronary angiography, and biochemical indicators are collected from patients with dilated cardiomyopathy, coronary heart disease and heart failure, and healthy individuals. The expressions of miR-126-5p and PECAM-1 mRNA, and PECAM-1 protein tyrosine phosphorylation in peripheral blood endothelial cells are measured in all participants.

The clinical data of the dilated cardiomyopathy group, the coronary heart disease (CHD) with heart failure group, and the control group are shown in FIG. 1, where panel A is echocardiography, panel B is cardiac ejection fraction (EF), panel C is left ventricular diameter (LV), and panel D is serum NT-proBNP. Compared with the normal control group, patients with dilated cardiomyopathy and patients with CHD with heart failure show significantly decreased ejection fraction (EF), significantly increased left ventricular (LV) diameter, and significantly elevated NT-proBNP levels. However, in the dilated cardiomyopathy group, when patients are diagnosed with dilated cardiomyopathy after coronary angiography ruled out coronary heart disease, the EF of the patients with the dilated cardiomyopathy is further reduced compared with the patients with CHD with heart failure, and the LV diameter is further increased.

The exemplary steps for detecting the expressions of miR-126-5p and PECAM-1 mRNA, and PECAM-1 protein tyrosine phosphorylation in peripheral blood endothelial cells are as follows.

1 Isolation and Extraction of Endothelial Cells from Peripheral Blood:

Collecting 20 ml of peripheral blood and isolating PBMCs using density gradient centrifugation. Specifically, after taking the peripheral whole blood, diluting the whole blood sample with PBS at a volume ratio of 1:1 of the whole blood sample to PBS, mixing them well to form a mixture solution, and then slowly adding the mixture solution to the upper layer of a cell isolation medium at a volume ratio of 1:1 of the mixture solution to the cell isolation medium, and performing the gradient centrifugation at room temperature with parameters of rotation 2300 rpm/min, acceleration 9, deceleration 0, and centrifugation time 20 min. After centrifugation, taking the white cells in the middle layer, adding PBS to the white cells to dilute and wash, and centrifuging it again (1680 rpm/min, centrifugation for 10 min), wherein the white precipitate is PBMCs.

Resuspending PBMCs with a certain amount of PBS (concentrating 10 times according to the original blood sample volume), taking 300 μL of the PBMC suspension, and adding CD45 antibody/magnetic beads (e.g., 1-5 μg CD45 antibody is added to 25-50 μL of magnetic beads at a concentration of 1 mg/mL to form CD45 antibody-conjugated magnetic beads) to the PBMC suspension sample and incubating them in a 360° rotating apparatus at room temperature for 1-2 hours, thereby forming a precipitate complex of leukocytes (including lymphocytes and B cells) in the CD45 antibody/magnetic bead-conjugated PBMCs, leukocytes, and the CD45 antibody/magnetic beads conjugation. A magnetic rack is used to precipitate and capture the CD45 antibody/magnetic bead-conjugated leukocytes in the PBMCs. The precipitation is extracted, and the supernatant is collected. At this point, the supernatant also contains a small number of other mononuclear cells including endothelial cells. Specific CD31 antibody (1-2 μL) is mixed with magnetic beads (1 mg/mL, 25-50 μL) to conjugate the CD31 antibody onto the magnetic beads to form CD31 antibody/magnetic beads. This mixture is then suspended with the supernatant and incubated overnight in a 360° rotating apparatus. The CD31 antibody/magnetic beads capture peripheral blood endothelial cells, thereby yielding the desired sample for testing.

2. Detection of miR-126-5p and PECAM-1 mRNA in Peripheral Blood Endothelial Cells:

① Extraction of Total RNA from Peripheral Blood Endothelial Cells:

First, after obtaining the endothelial cells, adding 350 μL of RNA lysis buffer (RLA) and 10 μL of proteinase K in the obtained endothelial cells to form a suspension, vortex oscillating the suspension, and centrifuging the suspension at 12000 rpm for 5 min (4° C.), and collecting the supernatant. Adding the supernatant to a genomic DNA removal column, centrifuging at 12000 rpm for 30 s (4° C.), retaining the filtrate, and slowly adding 70% ethanol with 1 time volume of the supernatant to the supernatant, and mixing it well (precipitation may occur at this point) to form a mixture thereof.

Then, transferring the mixture and the precipitation together into an RNase-Free adsorption column CR4 (the adsorption column is placed in a collection tube), centrifuging it at 12000 rpm for 30 s (4° C.), discarding the waste liquid in the collection tube, adding 700 μL of protein removal buffer RW3 to the adsorption column CR4, centrifuge at 12000 rpm for 30 s (4° C.), and discarding the waste liquid. Next, adding 500 μL of wash buffer RW to the adsorption column CR4, letting stand at room temperature for 2 min, centrifuging at 12000 rpm for 60 s (4° C.), discarding the waste liquid, and repeating this step once. Thereafter, centrifuging it at 12000 rpm for 2 min (4° C.), and discarding the waste liquid.

Finally, letting the RNase-Free adsorption column CR4 stand at room temperature for 2 min, allowing the wash buffer to dry completely, adding 30-100 μL of RNase-free $dH_2O$, letting it stand at room temperature for 2 min, centrifuging it at 12000 rpm for 2 min (4° C.) to obtain the total RNA solution, and storing it on ice for later use.

RNA purity and concentration detection: taking 2 μL of the above total RNA solution, diluting the total RNA solution at a certain factor with RNase-free ddH2O, and measuring its $OD_{260}/OD_{280}$ optical density ratio (>1.8 indicates high sample purity) and concentration using a microplate reader.

RNA Concentration Calculation:

$$\text{Final concentration}(ng/\mu L)=(OD_{260})\times(\text{dilution factor } n)\times 40.$$

② RNA Reverse Transcription to cDNA (Ice-Based Operation):

Reverse transcription is performed to synthesize cDNA for miR-126-5p and PECAM-1 mRNA, respectively.

For miR-126-5p reverse transcription to synthesize cDNA, first, removing genomic DNA. Specifically, adding 1.0 μL of gDNA remover, 1.0 μL of 10×gDNA eraser buffer, 5 μL of total RNA, and 3.0 μL of RNase-free $dH_2O$, totally 10 μL solution; gently mixing and centrifuging it; and then reacting at 37° C. for 2 min, then cooling and storing it on ice. The reverse transcription system includes 4.0 μL of 5×PrimerScript buffer, 2.0 μL of reverse transcription primers, SweScript RT II Enzyme Mix, 4.0 μL of Nuclease-Free Water, and 10 μL of the reaction solution used to remove genomic DNA in the previous steps, totally a 20 μL mixture. The reaction conditions are 25° C. for 15 min, 55° C. for 15 min, 85° C. for 5 s, and storage at 4° C.

The internal control for miR-126-5p is U6. The reverse transcription primers included miR-126-5p-RT and U6-A, with nucleotide sequences shown in SEQ ID NO. 1 and SEQ ID NO. 2, respectively.

miR-126-5p-RT: CTCAACTGGTGTCGTGGAGTCGGCAATTCAGTTGAGCGCGTACC (SEQ ID NO. 1),

U6-A: AACGCTTCACGAATTTGCGT (SEQ ID NO. 2).

For PECAM-1 mRNA, cDNA is synthesized by reverse transcription. The reverse transcription kit used is: NovoScript®Plus All-in-one 1st Strand cDNA Synthesis SuperMix (gDNA Purge) (Cat. No.: E047). The reverse transcription system includes: gDNA Remover, 1.0 μL, the total RNA, 6.0 μL, SweScript RT II Enzyme Mix, 10.0 μL, and Nuclease-Free Water, 3.0 μL, totally a 20 μL mixture. The reaction conditions are: 50° C. for 15 min, 85° C. for 5 s, and storage at 4° C. The internal control for PECAM-1 mRNA is GAPDH.

③ Detection of miR-126-5p and PECAM-1 mRNA Expression Levels by Quantitative Real-Time PCR (qPCR):

After obtaining the corresponding template cDNA, quantitative real-time PCR is performed using SYBR Premix Ex Taq™ (TaKaRa Biotech Co., Ltd.) reagents. The mRNA levels of miR-126-5p and PECAM-1 are detected using the Bio-Rad Real-Time PCR System. The qPCR reaction system is as follows:

SYBR Premix Ex Taq™II (2×), 10.0 μL,
PCR upstream primer (10 μM), 1.0 μL,
PCR downstream primer (10 μM), 1.0 μL,
cDNA template, 1.0 μL,
RNase free $dH_2O$, 7.0 μL,
Total volume, 20.0 μL.

The reaction conditions are: pre-denaturation: 95° C., 30s; PCR reaction: 95° C., 5s, 60° C., 34s, for a total of 40 cycles. Melting curve: 95° C., 15s, 60° C., 1 min, 95° C., 15s.

The amplification primer for miR-126-5p is miR-126-5p-S and universal primer-A, with nucleotide sequences shown in SEQ ID NO. 3 and SEQ ID NO. 4, respectively.

miR-126-5p-S: ACACTCCAGCTGGGCATTATTACTTTTGG (SEQ ID NO. 3),

Universal primer-A: TGGTGTCGTGGAGTCG (SEQ ID NO. 4).

The amplification primer for the internal control U6 of miR-126-5p are U6-S and U6-A, with nucleotide sequences shown in SEQ ID NO. 5 and SEQ ID NO. 2, respectively.

U6-S: CTCGCTTCGGCAGCACA (SEQ ID NO. 5),

U6-A: AACGCTTCACGAATTTGCGT (SEQ ID NO. 2).

The amplification primer for PECAM-1 mRNA are H-pecam1-S and H-pecam1-A, with nucleotide sequences shown in SEQ ID NO. 6 and SEQ ID NO. 7, respectively.

H-pecam 1-S: AACTTAACAGAACTGTTTCCCAG (SEQ ID NO. 6),

H-pecam1-A: GCATCTTGCTGAAAATTCTGATACT (SEQ ID NO. 7).

The amplification primer for the internal control GAPDH of PECAM-1 mRNA are H-GAPDH-S and H-GAPDH-A, with nucleotide sequences shown in SEQ ID NO. 8 and SEQ ID NO. 9, respectively.

H-GAPDH-S: GGAAGCTTGTCATCAATGGAAATC (SEQ ID NO. 8),

H-GAPDH-A: TGATGACCCTTTTGGCTCC (SEQ ID NO. 9).

The results of quantitative real-time PCR are the number of cycles (expressed as Ct values) required for the fluorescence signal in each reaction tube to reach the set threshold, where ΔCt=Ct (target gene)-Ct (internal reference), ΔΔCt=ΔCt (experimental group)-ΔCt (control), Relative expression level=$2^{-\Delta\Delta Ct}$, The control is any randomly selected healthy individual.

The relative expression level of miR-126-5p is the expression level of miR-126-5p relative to the internal control gene U6, and the relative expression level of PECAM-1 mRNA is the expression level of PECAM-1 mRNA relative to the internal control GAPDH.

Figure 2:
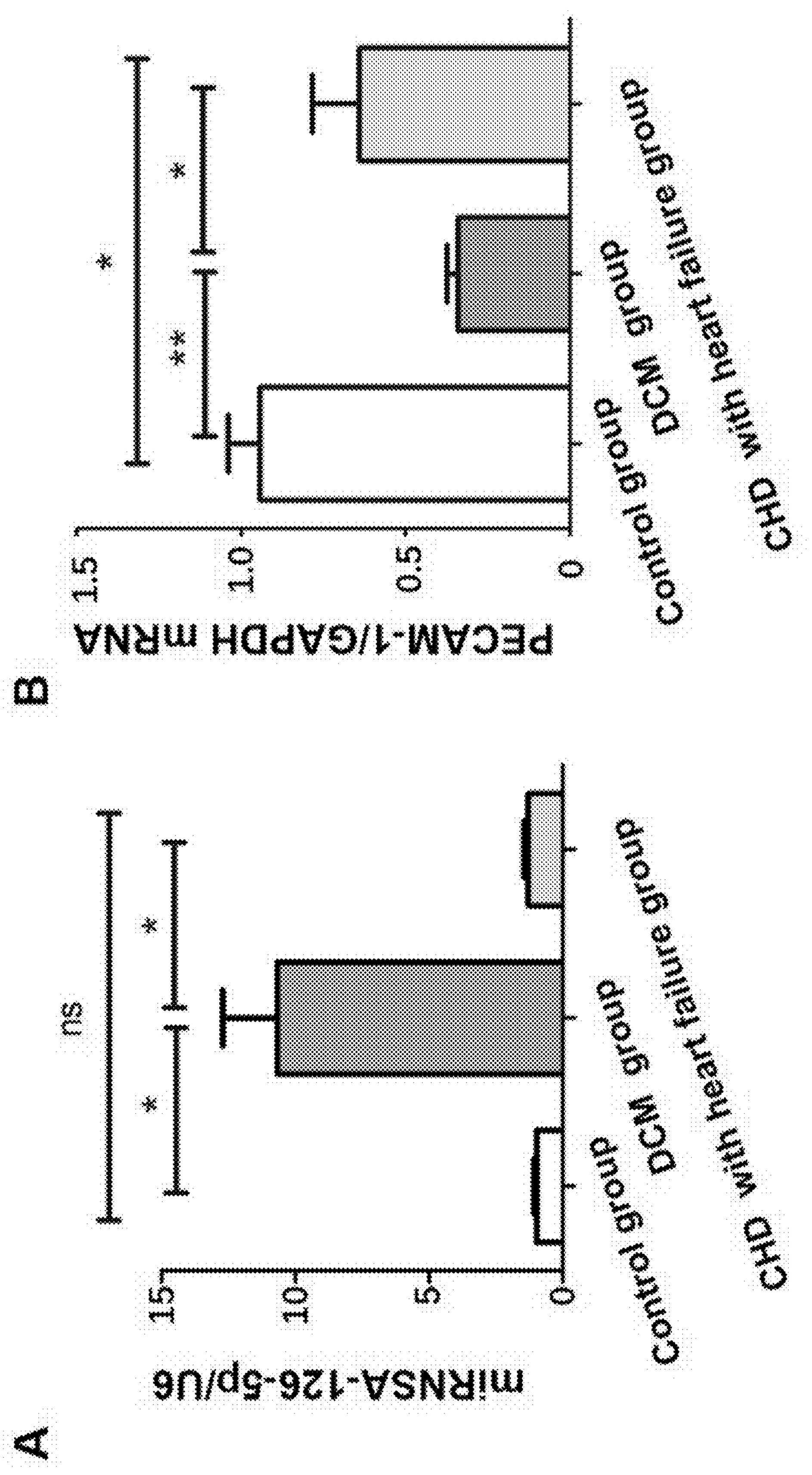
FIG. 2 shows the expression levels of miR-126-5p (panel A) and of PECAM-1 mRNA (panel B) in the peripheral blood endothelial cells of the control group, the dilated cardiomyopathy group, and the coronary heart disease and heart failure group according to Embodiment 1 of the invention.

The results are shown in FIG. 2. Panel A of FIG. 2 shows the expression levels of miR-126-5p in the control group, the dilated cardiomyopathy group, and the coronary heart disease/heart failure group. The expression level of miR-126-5p in the patients with the dilated cardiomyopathy is several hundred times higher than that in the control group and the coronary heart disease/heart failure group, significantly higher than both groups ($P<0.05$). As shown in penal B of FIG. 2, the expression levels of PECAM-1 mRNA in the patients with the dilated cardiomyopathy and the control group. The expression level of PECAM-1 mRNA in the patients with the dilated cardiomyopathy is significantly lower than that in the control group and the coronary heart disease/heart failure group.

Compared with the normal control group, the susceptibility gene miR-126-5p is highly expressed in the endothelial cells of patients with dilated cardiomyopathy under oxidative stress, and the expression level of miR-126-5p is significantly higher than that in the control group. As a target gene of miR-126-5p, overexpression of miR-126-5p inhibits the production of PECAM-1 mRNA. PECAM-1 mRNA levels in the patients with the dilated cardiomyopathy are significantly lower than in the control group, accompanied by exacerbation of heart failure at the same time. The experimental results also indicate that the occurrence of the dilated cardiomyopathy is closely related to the individual patient's susceptibility to oxidative stress response to miR-126-5p gene.

3. Detection of PECAM-1 Protein Tyrosine Phosphorylation Level in Peripheral Blood Endothelial Cells:

After collecting endothelial cells captured by CD31-coupled magnetic beads, a certain amount of RIPA high-efficiency lysis buffer (containing Cocktail—a protease inhibito, PMSF (phenylmethylsulfonyl fluoride), and phosphatase inhibitor) is added. Lysis is performed on ice for 20 min, followed by centrifugation at 12000 rpm for 10 min (4° C.). The supernatant is collected, and the protein concentration is determined using the BCA method. 5×SDS-PAGE loading buffer is added to the complex sample (i.e., adding 1 volume of loading buffer to 4 volumes of the complex sample, having a total volume of 5, the complex sample can be a mixture of protein and lysis buffer for example), and the mixture is thoroughly mixed and heated at 95° C. for 5 min for denaturation before subsequent SDS-PAGE detection.

SDS-PAGE detection: An 11-well 8% separating gel is prepared. 30 μL of the denatured sample is loaded and subjected to SDS-PAGE electrophoresis. For example, the denatured sample is obtained by boiling the protein lysis buffer with added loading buffer. The parameters are set as follows: 80V electrophoresis for 30 min, followed by constant voltage electrophoresis at 120V for 60-90 min. After electrophoresis, the SDS-PAGE separating gel is used for transfer to a PVDF (polyvinylidene fluoride) membrane (pretreated by soaking in methanol and activating for 10 min). Transfer parameters: constant current 250 mA, 2-2.5 h. After transferred, the PVDF membrane is blocked in 5% BSA (bovine serum albumin) or skim milk blocking buffer for 1 h, then incubated overnight with phosphorylated tyrosine antibody (the volume ratio of the antibody to diluent is 1:50-1:250). After primary antibody recovery, the membrane is washed three times with TBST (Tris-buffered saline with addition of Tween 20, 8 min/wash), incubated with the corresponding secondary antibody (room temperature incubation for 1 h), washed three times with TBST, and then developed with chemiluminescence.

The expression level of PECAM-1 protein tyrosine phosphorylation is determined according to Marker molecular weight. Using the image analysis function of the Bio-Rad protein expression analysis system, select the MW (Molecular Weight) analysis tool, which is usually used for analyzing protein molecular weight and grayscale values in protein electrophoresis experimental data, select the target band, and click the analysis table to obtain the corresponding gray value.

β-actin is used as an internal control. The ratio of the gray value of PECAM-1 protein tyrosine phosphorylation to that of β-actin is used as the relative expression level of PECAM-1 protein tyrosine phosphorylation. The PECAM-1 protein tyrosine phosphorylation level can also be directly measured using the external standard method.

Figure 3:
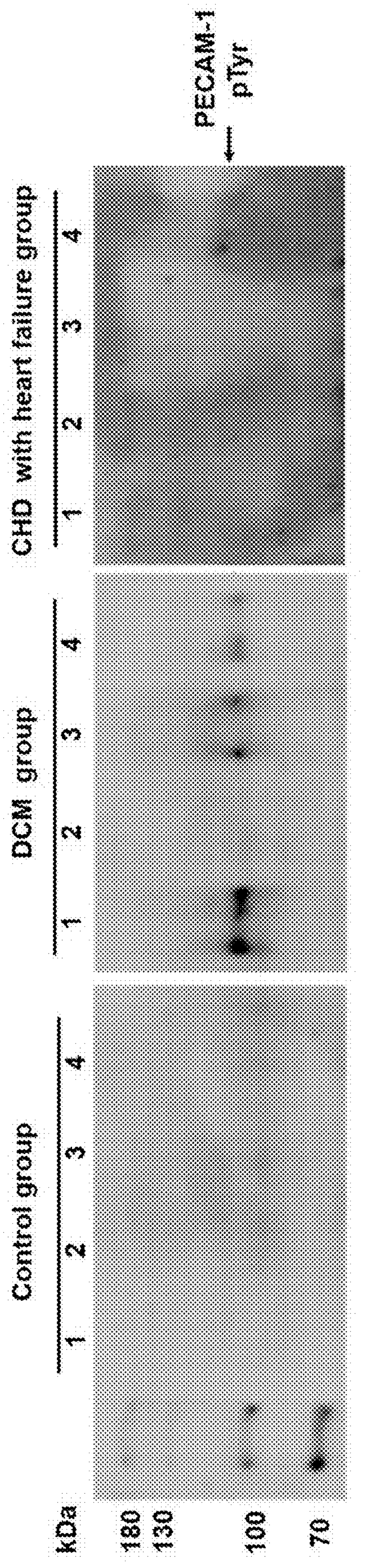
FIG. 3 shows the results of Western blot analysis of the tyrosine phosphorylation of PECAM-1 protein in the peripheral blood endothelial cells of the control group, the dilated cardiomyopathy group, and the coronary heart disease and heart failure group according to Embodiment 1 of the invention.
Figure 4:
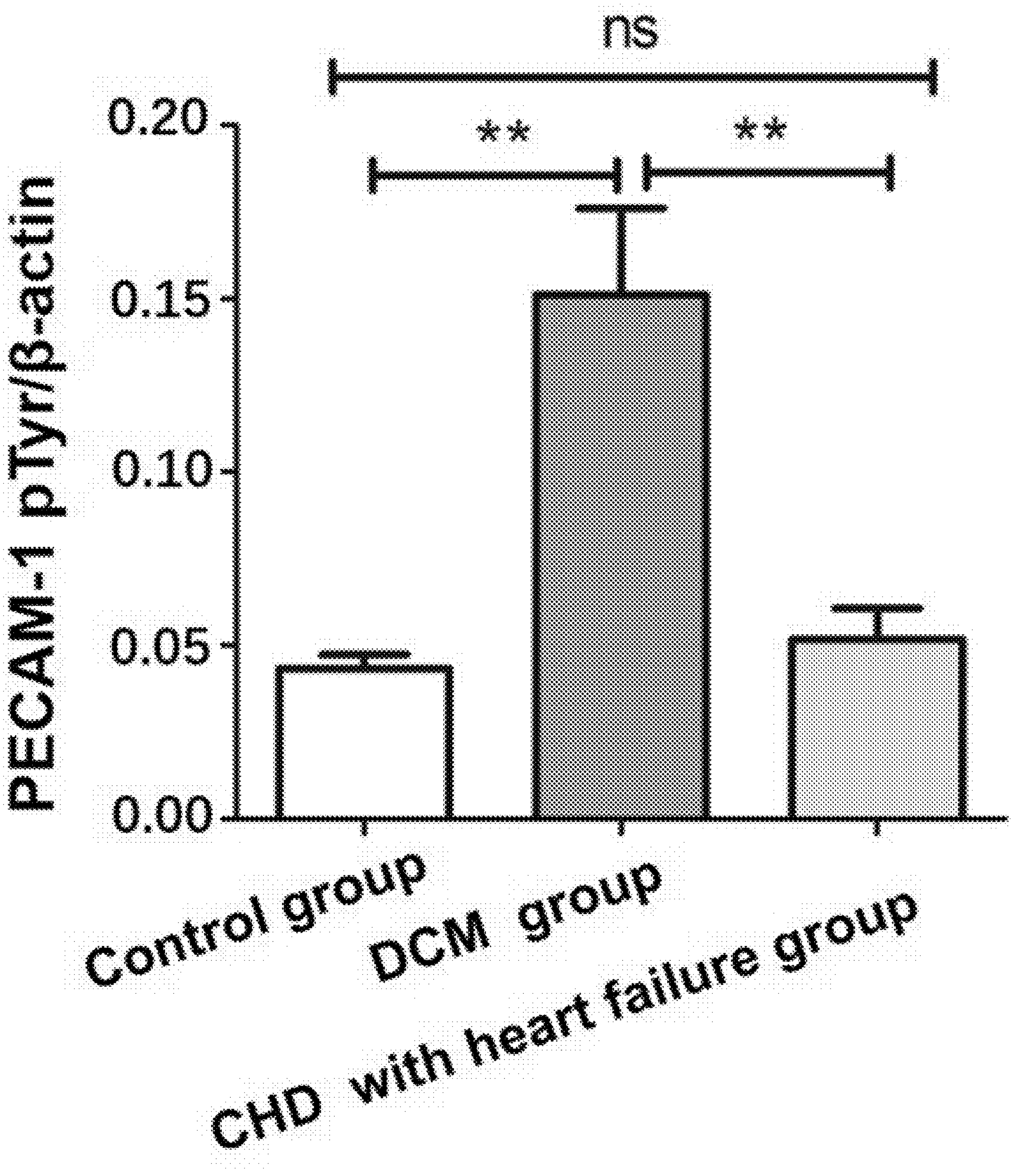
FIG. 4 shows the ratio of the tyrosine phosphorylation of PECAM-1 protein to the internal control in the peripheral blood endothelial cells of the control group, the dilated cardiomyopathy group, and the coronary heart disease and heart failure group according to Embodiment 1 of the invention.

The results of the PECAM-1 protein tyrosine phosphorylation in the control group and the dilated cardiomyopathy group are shown in FIGS. 3 and 4. The gray value of the PECAM-1 protein tyrosine phosphorylation signal (relative to the internal control β-actin) in peripheral blood endothelial cells of the patients with the dilated cardiomyopathy is significantly higher than that in the control group, with an increase of about 1.4-3.5 times. This result indicates that the expression level of PECAM-1 protein tyrosine phosphorylation in the peripheral blood endothelial cells is upregulated in the patients with the dilated cardiomyopathy, while cardiac function is reduced.

In brief, compared with the control group and the coronary heart disease and heart failure group, the expression level of miR-126-5p in the peripheral blood endothelial cells of the patients with the dilated cardiomyopathy is significantly increased, the PECAM-1 mRNA level is decreased, and the PECAM-1 protein tyrosine phosphorylation level is significantly increased. The expression levels of miR-126-5p and PECAM-1 mRNA, as well as the PECAM-1 protein tyrosine phosphorylation level, are all significantly different, compared with healthy individuals and the patients with coronary heart disease and heart failure. The combination of PECAM-1 protein tyrosine phosphorylation level with miR-126-5p or PECAM-1 protein tyrosine phosphorylation level with miR-126-5p and PECAM-1 mRNA can be used as a biomarker combination for the preparation of a dilated cardiomyopathy diagnostic kit. This kit can distinguish dilated cardiomyopathy from healthy individuals, and can also effectively differentiate between dilated cardiomyopathy and patients with coronary heart disease and heart failure.

Embodiment 2

In this embodiment, the dilated cardiomyopathy diagnostic kit comprises peripheral blood endothelial cell isolation and extraction reagents, miR-126-5p reverse transcription primers, internal control U6 reverse transcription primers, internal control U6 amplification primers, primer pairs designed for amplifying the cDNA after miR-126-5p reverse transcription (the base sequence of the forward primer is shown in SEQ ID NO. 3, and the reverse primer is a universal reverse amplification primer, the base sequence of which is shown in SEQ ID NO. 4), protein isolation and purification reagents, and a protein immunoblotting detection reagent containing an anti-phosphorylated tyrosine antibody. The dilated cardiomyopathy diagnostic kit can detect the expression level of miR-126-5p and the tyrosine phosphorylation level of PECAM-1 protein in peripheral blood endothelial cells.

Embodiment 3

In this embodiment, the dilated cardiomyopathy diagnostic kit comprises peripheral blood endothelial cell isolation and extraction reagent, miR-126-5p reverse transcription primers, internal control U6 reverse transcription primers, internal control U6 amplification primers, primer pairs designed for amplifying the cDNA after miR-126-5p reverse transcription (the base sequence of the forward primer is shown in SEQ ID NO. 3, and the reverse primer is a universal reverse amplification primer, the base sequence of which is shown in SEQ ID NO. 4), protein isolation and purification reagents, a protein immunoblotting detection reagent containing an anti-phosphorylated tyrosine antibody, PECAM-1 mRNA amplification primers, and internal control GAPDH amplification primers. The dilated cardiomyopathy diagnostic kit can detect the expression levels of miR-126-5p and PECAM-1 mRNA and the tyrosine phosphorylation level of PECAM-1 protein in peripheral blood endothelial cells.

Test Examples

Blood samples from 32 patients with dilated cardiomyopathy, 32 patients with coronary artery disease and heart failure, and 30 healthy individuals are used as test samples, with each sample is analyzed at least three times. Dilated cardiomyopathy is detected using the dilated cardiomyopathy diagnostic kits of EMBODIMENT 2 (simultaneous miR-126-5p and PECAM-1 protein tyrosine phosphorylation levels as the biomarkers) and EMBODIMENT 3 (simultaneous miR-126-5p, PECAM-1 mRNA, and PECAM-1 as the biomarkers), respectively.

The biomarkers are detected in healthy individuals, patients with coronary heart disease and heart failure, and patients with dilated cardiomyopathy using the dilated cardiomyopathy diagnostic kits of EMBODIMENT 2 and EMBODIMENT 3, respectively. ROC (Receiver Operating Characteristic) analysis is performed using SPSS (Statistical Package for the Social Sciences, IBM) software to obtain the ROC analysis results, and the mean AUC (Area Under the Curve), sensitivity, and specificity are calculated. The sensitivity and specificity are calculated as follows:

When using miR-126-5p expression level and PECAM-1 protein tyrosine phosphorylation level from EMBODIMENT 2, or miR-126-5p, PECAM-1 mRNA expression level, and PECAM-1 protein tyrosine phosphorylation level from EMBODIMENT 3 as the biomarkers, a binary or multivariate logistic regression analysis is first performed on the data for multiple biomarkers to obtain a probability value. Then, ROC analysis is performed using the probability value as the test variable. The sensitivity is the proportion of positive cases in dilated cardiomyopathy (DCM) samples. When the statistical analysis is performed using three groups: DCM, coronary artery disease with heart failure, and healthy individuals, the specificity is the proportion of negative DCM cases in healthy individuals and coronary artery disease/heart failure samples. When statistical analysis is performed using two groups: DCM and healthy individuals, the specificity is the proportion of negative DCM cases in healthy individuals.

The ROC results for diagnosing dilated cardiomyopathy in healthy individuals and patients with dilated cardiomyopathy are shown in Table 1 below.

TABLE 1

ROC results for diagnosing DCM in healthy individuals and patients with DCM

| Diagnostic kit | Detected biomarkers | Sensitivity | Specificity | AUC | 95% confidence interval |
|---|---|---|---|---|---|
| EMBODIMENT 2 | miR-126-5p, PECAM-1 protein tyrosine phosphorylation level | 86.2% | 97% | 0.949 | 0.867~1.000 |
| EMBODIMENT 3 | miR-126-5p, PECAM-1 protein tyrosine phosphorylation level, PECAM-1 mRNA expression level | 93.1% | 93.7% | 0.978 | 0.874~1.000 |

The ROC results for diagnosing dilated cardiomyopathy in three group: healthy individuals, patients with coronary heart disease and heart failure, and patients with dilated cardiomyopathy, are shown in Table 2 below.

TABLE 2

ROC results for diagnosis of DCM in three groups, healthy individuals, patients with coronary heart disease and heart failure, and patients with DCM

| Diagnostic kit | Detected biomarkers | Sensitivity | Specificity | AUC | 95% confidence interval |
|---|---|---|---|---|---|
| EMBODIMENT 2 | miR-126-5p, PECAM-1 protein tyrosine | 86.2% | 96.8% | 0.953 | 0.895~1.000 |

TABLE 2-continued

ROC results for diagnosis of DCM in three groups, healthy individuals, patients with coronary heart disease and heart failure, and patients with DCM

| Diagnostic kit | Detected biomarkers | Sensitivity | Specificity | AUC | 95% confidence interval |
|---|---|---|---|---|---|
| EMBODIMENT 3 | phosphorylation level miR-126-5p, PECAM-1 protein tyrosine phosphorylation level, PECAM-1 mRNA expression level | 93.1% | 93.7% | 0.981 | 0.897~1.000 |

The diagnostic kit in EMBODIMENT 2 (using miR-126-5p and PECAM-1 protein tyrosine phosphorylation as biomarkers for dilated cardiomyopathy) shows the sensitivity and specificity of about 86.2% and about 96.8% in distinguishing dilated cardiomyopathy from healthy individuals and patients with coronary heart disease and heart failure, respectively, with the AUC of about 0.953. The diagnostic kit in EMBODIMENT 3 further includes the biomarker PECAM-1 mRNA. The kit shows the sensitivity and specificity of about 93.1% and about 93.7% in distinguishing dilated cardiomyopathy from healthy individuals and patients with coronary heart disease and heart failure, respectively, with the AUC of about 0.981. The diagnostic kit in EMBODIMENT 3 shows the sensitivity and specificity of about 93.1% and about 93.7% in distinguishing dilated cardiomyopathy from healthy individuals and patients with coronary heart disease and heart failure, respectively, with the AUC of about 0.978. Compared to EMBODIMENT 2, although the specificity decreased slightly, both the sensitivity and AUC are further improved.

As shown in Tables 1 and 2, the diagnostic kit in EMBODIMENT 2 exhibits similar sensitivity and specificity in distinguishing between patients with dilated cardiomyopathy and healthy individuals, as well as between patients with dilated cardiomyopathy, healthy individuals, and patients with coronary heart disease and heart failure. Similarly, the diagnostic kit in EMBODIMENT 3 shows similar sensitivity and specificity in distinguishing between patients with dilated cardiomyopathy and healthy individuals, as well as between patients with dilated cardiomyopathy, healthy individuals, and patients with coronary heart disease and heart failure. This indicates that both the diagnostic kits based on the combination of miR-126-5p and PECAM-1 protein tyrosine phosphorylation biomarkers in EMBODIMENT 2 and the detection kit based on the combination of miR-126-5p, PECAM-1 protein tyrosine phosphorylation, and PECAM-1 mRNA biomarkers in EMBODIMENT 3 can distinguish between dilated cardiomyopathy samples and healthy samples, and also between dilated cardiomyopathy samples and coronary heart disease samples with high specificity and sensitivity.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described to explain the principles of the invention and their practical application to enable others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

What is claimed is:

1. A diagnostic kit for detecting dilated cardiomyopathy, comprising:

a cell isolation and extraction reagent comprising CD45-conjugated magnetic beads and CD31-conjugated magnetic beads configured to sequentially deplete CD45-positive leukocytes and capture CD31-positive endothelial cells from a peripheral blood sample;

a first detection reagent comprising a primer pair designed for amplifying cDNA after reverse transcription of miR-126-5p, wherein the primer pair comprises a forward primer having the nucleotide sequence of SEQ ID NO: 3 and a reverse primer having the nucleotide sequence of SEQ ID NO: 4; and a second detection reagent comprising an anti-phosphotyrosine antibody reagent configured to detect tyrosine-phosphorylated PECAM-1 protein;

wherein the cell isolation and extraction reagent, the first detection reagent, and the second detection reagent are adapted in a kit configuration to enable concurrent detection of miR-126-5p expression and PECAM-1 protein tyrosine phosphorylation in the captured endothelial cells.

2. The kit of claim 1, wherein the cell isolation and extraction reagent further comprises a concentration buffer configured to concentrate peripheral blood mononuclear cells (PBMCs) at least 10-fold relative to an original blood volume prior to incubation with the CD45-conjugated magnetic beads, thereby increasing an endothelial cell yield to a detectable threshold for the first detection reagent and the second detection reagent.

3. The kit of claim 1, wherein the anti-phosphotyrosine antibody reagent comprises a monoclonal antibody that specifically binds a phosphotyrosine epitope of PECAM-1 protein for use in a protein immunoblotting assay.

4. The kit of claim 1, further comprising one or more of an RNA extraction reagent, an RNA reverse transcription reagent, and a real-time quantitative PCR reagent, which are pre-calibrated for use with the captured endothelial cells to detect miR-126-5p and PECAM-1 mRNA.

5. The kit of claim 1, further comprising a first internal control reagent comprising U6 primers for normalizing miR-126-5p expression levels; and a second internal control reagent comprising a β-actin antibody for normalizing PECAM-1 protein tyrosine phosphorylation levels.

6. The kit of claim 1, further comprising a third detection reagent comprising a primer pair configured to amplify PECAM-1 mRNA.

7. The kit of claim 6, wherein the kit is configured to enable simultaneous quantification of miR-126-5p expression, PECAM-1 mRNA expression, and PECAM-1 protein tyrosine phosphorylation levels from the captured endothelial cells.

8. The kit of claim 6, wherein the third detection reagent is configured to operate in parallel with the first detection reagent and the second detection reagent using standardized reagent volumes pre-optimized for low-yield endothelial cell lysates.

9. The kit of claim 6, further comprising a third internal control reagent comprising GAPDH primers for normalizing PECAM-1 mRNA expression levels.

10. The kit of claim 6, further comprising instruction materials directing a user to apply the kit to diagnose dilated cardiomyopathy by comparing normalized expression levels of miR-126-5p, PECAM-1 mRNA, and tyrosine-phosphorylated PECAM-1 against standardized control thresholds.

* * * * *

SEQUENCE LISTING

```
Sequence total quantity: 9
SEQ ID NO: 1            moltype = DNA  length = 44
FEATURE                 Location/Qualifiers
source                  1..44
                        mol_type = other DNA
                        organism = synthetic construct
SEQUENCE: 1
ctcaactggt gtcgtggagt cggcaattca gttgagcgcg tacc                  44

SEQ ID NO: 2            moltype = DNA  length = 20
FEATURE                 Location/Qualifiers
source                  1..20
                        mol_type = other DNA
                        organism = synthetic construct
SEQUENCE: 2
aacgcttcac gaatttgcgt                                             20

SEQ ID NO: 3            moltype = DNA  length = 29
FEATURE                 Location/Qualifiers
source                  1..29
                        mol_type = other DNA
                        organism = synthetic construct
SEQUENCE: 3
```

-continued

```
acactccagc tgggcattat tacttttgg                                    29

SEQ ID NO: 4            moltype = DNA  length = 16
FEATURE                 Location/Qualifiers
source                  1..16
                        mol_type = other DNA
                        organism = synthetic construct
SEQUENCE: 4
tggtgtcgtg gagtcg                                                  16

SEQ ID NO: 5            moltype = DNA  length = 17
FEATURE                 Location/Qualifiers
source                  1..17
                        mol_type = other DNA
                        organism = synthetic construct
SEQUENCE: 5
ctcgcttcgg cagcaca                                                 17

SEQ ID NO: 6            moltype = DNA  length = 23
FEATURE                 Location/Qualifiers
source                  1..23
                        mol_type = other DNA
                        organism = synthetic construct
SEQUENCE: 6
aacttaacag aactgtttcc cag                                          23

SEQ ID NO: 7            moltype = DNA  length = 26
FEATURE                 Location/Qualifiers
source                  1..26
                        mol_type = other DNA
                        organism = synthetic construct
SEQUENCE: 7
gcaatcttgc tgaaaattct gatact                                       26

SEQ ID NO: 8            moltype = DNA  length = 24
FEATURE                 Location/Qualifiers
source                  1..24
                        mol_type = other DNA
                        organism = synthetic construct
SEQUENCE: 8
ggaagcttgt catcaatgga aatc                                         24

SEQ ID NO: 9            moltype = DNA  length = 19
FEATURE                 Location/Qualifiers
source                  1..19
                        mol_type = other DNA
                        organism = synthetic construct
SEQUENCE: 9
tgatgaccct tttggctcc                                               19
```